(12) United States Patent
Fujita et al.

(10) Patent No.: US 9,687,435 B2
(45) Date of Patent: Jun. 27, 2017

(54) CALCIUM PHOSPHATE DISPERSION COMPOSITION

(71) Applicant: KABUSHIKI KAISHA SANGI, Tokyo (JP)

(72) Inventors: Keijiro Fujita, Tokyo (JP); Mariko Obuki, Tokyo (JP); Tomoki Saito, Tokyo (JP); Shuji Sakuma, Tokyo (JP)

(73) Assignee: KABUSHIKI KAISHA SANGI, Tokyo (JP)

( * ) Notice: Subject to any disclaimer, the term of this patent is extended or adjusted under 35 U.S.C. 154(b) by 0 days.

(21) Appl. No.: 14/375,562

(22) PCT Filed: Jan. 28, 2013

(86) PCT No.: PCT/JP2013/000433
§ 371 (c)(1),
(2) Date: Jul. 30, 2014

(87) PCT Pub. No.: WO2013/118452
PCT Pub. Date: Aug. 15, 2013

(65) Prior Publication Data
US 2015/0010481 A1    Jan. 8, 2015

(30) Foreign Application Priority Data
Feb. 7, 2012    (JP) .................. 2012-024465

(51) Int. Cl.
| | | |
|---|---|---|
| *A61K 8/24* | (2006.01) | |
| *A61K 8/73* | (2006.01) | |
| *A23L 2/52* | (2006.01) | |
| *A61Q 11/00* | (2006.01) | |
| *A61K 47/14* | (2017.01) | |
| *A61K 47/18* | (2017.01) | |
| *A61K 47/36* | (2006.01) | |
| *A61K 33/42* | (2006.01) | |
| *A61K 9/00* | (2006.01) | |
| *A23C 9/13* | (2006.01) | |
| *A23C 9/152* | (2006.01) | |
| *A61K 8/39* | (2006.01) | |
| *A61K 8/34* | (2006.01) | |
| *A61K 8/37* | (2006.01) | |
| *A23L 29/10* | (2016.01) | |
| *A23L 29/269* | (2016.01) | |
| *A23L 33/16* | (2016.01) | |

(52) U.S. Cl.
CPC .............. *A61K 8/73* (2013.01); *A23C 9/1322* (2013.01); *A23C 9/1522* (2013.01); *A23L 2/52* (2013.01); *A23L 29/10* (2016.08); *A23L 29/27* (2016.08); *A23L 33/16* (2016.08); *A61K 8/24* (2013.01); *A61K 8/345* (2013.01); *A61K 8/37* (2013.01); *A61K 8/39* (2013.01); *A61K 9/0053* (2013.01); *A61K 33/42* (2013.01); *A61K 47/14* (2013.01); *A61K 47/18* (2013.01); *A61K 47/36* (2013.01); *A61Q 11/00* (2013.01); *A61K 2800/92* (2013.01)

(58) Field of Classification Search
CPC ................................ A61K 33/06; A61K 33/42
See application file for complete search history.

(56) References Cited

U.S. PATENT DOCUMENTS

| | | | |
|---|---|---|---|
| 4,910,026 A | | 3/1990 | Hugelshofer |
| 5,035,881 A | * | 7/1991 | Mori ................ A61K 8/43 424/49 |
| 5,178,869 A | * | 1/1993 | Ebine .............. A61K 8/4926 222/192 |
| 6,074,675 A | * | 6/2000 | Nanbu .............. A21D 2/02 426/52 |
| 2004/0009235 A1 | * | 1/2004 | Li ................... A61K 9/1617 424/602 |
| 2004/0022747 A1 | * | 2/2004 | Fisher .............. A61K 8/19 424/52 |
| 2006/0013921 A1 | * | 1/2006 | Kasahara et al. ........... 426/74 |

(Continued)

FOREIGN PATENT DOCUMENTS

| | | |
|---|---|---|
| EP | 0786245 | 7/1997 |
| JP | 63-263062 | 10/1988 |

(Continued)

OTHER PUBLICATIONS

Partial Translation of JP H11-199456 A.*
"Devil's Food Premium Cake Mix," Aug. 1, 2005, Database Accession No. 389005.
"Smoo Cake Foundation," Apr. 1, 2010, Database Accession No. 1310862.
"Sunproof Lipstick SPF15," Jul. 1, 2011, Database Accession No. 1593045.

*Primary Examiner* — Frederick Krass
*Assistant Examiner* — Amanda Heyes
(74) *Attorney, Agent, or Firm* — Occhiuti & Rohlicek LLP

(57) ABSTRACT

It is intended to provide a liquid oral composition and a liquid food composition in which calcium phosphate such as hydroxyapatite or tricalcium phosphate can be stably dispersed and prevented from being precipitated or separated out even in long-term storage. Calcium phosphate mixed with xanthan gum and polyglycerin fatty acid ester can be stably dispersed even in long-term storage and prevented from being precipitated or separated out even when used in liquid oral compositions such as mouthwashes, liquid dentifrices, and oral detergents or in liquid food compositions such as milk, soy milk, yoghurt, and refreshing beverages. In addition, calcium phosphate mixed with xanthan gum and polyglycerin fatty acid ester further supplemented with an amphoteric surfactant can be more effectively prevented from being precipitated or separated out in liquid oral compositions such as mouthwashes, liquid dentifrices, and oral detergents.

4 Claims, No Drawings

(56) References Cited

U.S. PATENT DOCUMENTS

| | | |
|---|---|---|
| 2006/0069062 A1* | 3/2006 | Shiomi et al. .................. 514/53 |
| 2009/0196942 A1 | 8/2009 | Goyarts et al. |

FOREIGN PATENT DOCUMENTS

| | | |
|---|---|---|
| JP | 04-217615 | 8/1992 |
| JP | 08-337518 | 12/1996 |
| JP | 09-202717 | 8/1997 |
| JP | 09-238645 | 9/1997 |
| JP | 11-199456 | 7/1999 |
| JP | 11199456 A * | 7/1999 |
| JP | 2000-093124 | 4/2000 |
| JP | 2000-157214 | 6/2000 |
| JP | 2001-031542 | 2/2001 |
| JP | 2004026658 | 1/2004 |
| JP | 2005-330269 | 12/2005 |
| JP | 2006-082985 | 3/2006 |
| JP | 2006-182662 | 7/2006 |
| JP | 2006/246900 | 9/2006 |
| JP | 2007-076995 | 3/2007 |
| JP | 2007-308422 | 11/2007 |
| JP | 2008-255305 | 10/2008 |
| JP | 2011-051927 | 3/2011 |
| WO | 98/14072 | 4/1998 |
| WO | 2004/039178 | 5/2004 |
| WO | 2004/054925 | 7/2004 |
| WO | 2009/091052 | 7/2009 |

* cited by examiner

CALCIUM PHOSPHATE DISPERSION COMPOSITION

CROSS REFERENCE TO RELATED APPLICATIONS

This application is a §371 National Stage of International Application No. PCT/JP2013/000433 filed on Jan. 28, 2013, which claims priority to Japanese Application No. 2012-024465 filed on Feb. 7, 2012, the contents of which are hereby incorporated by reference in their entirety.

TECHNICAL FIELD

The present invention relates to a composition that is excellent in the dispersion stability of calcium phosphate and that is capable of stably maintaining the dispersibility of the calcium phosphate in long-term storage. More specifically, the present invention relates to a calcium phosphate dispersion composition comprising calcium phosphate, xanthan gum, and polyglycerin fatty acid ester, and a liquid oral composition and a liquid food composition consisting of the calcium phosphate dispersion composition.

BACKGROUND ART

Dentifrices have heretofore been used for prevention of caries, prevention of bad breath, or oral cleansing. Such dentifrices, however, have poor usability because of their need for using a brush. Mouthwashes excellent in convenience have therefore become more popular in lifestyles and been widely used. These mouthwashes, however, are used for the purpose of keeping the mouth clean in such a way as to suppress the growth of harmful bacteria or prevent bad breath. Nonetheless, with changes in feelings for cleanliness or health, the mouthwashes have been demanded in recent years to have various functions including tooth whitening, tooth shining, and active contribution to the repair or health of teeth through remineralization action. In order to satisfy these demands, studies have been made on a mouthwash (patent documents 2 to 4) supplemented with hydroxyapatite (patent document 1), which is used as dentifrices and known to have the effects of promoting the remineralization of teeth and of whitening teeth.

Due to tendencies toward insufficient intakes of calcium, the intakes of calcium in necessary amounts in daily diets has been demanded in recent years. For example, foods such as milk, yoghurt, and refreshing beverages have been calcium-fortified actively. Upon addition of water-soluble calcium such as calcium lactate or calcium chloride as a calcium ingredient to dairy products such as milk or soy milk, the calcium ions react with proteins during thermal sterilization to precipitate the proteins. This phenomenon deteriorates taste and flavor and adversely affects the original taste of the foods. For these reasons, there is a ceiling to the addition of the water-soluble calcium. Recent studies have therefore been directed to, for example, a method which involves preparing fine particles of calcium carbonate or calcium phosphate, which is water-insoluble calcium, and dispersing the fine particles in foods by the addition of a dispersant. Unfortunately, calcium carbonate cannot be added in large amounts due to its bitterness. Again, the intakes of calcium in sufficient amounts cannot be achieved. Accordingly, if the dispersibility of calcium phosphate, particularly, a bone component hydroxyapatite, as a calcium ingredient can be stably maintained in water, various problems brought about by water-soluble calcium or calcium carbonate can be solved.

The water-insoluble calcium such as calcium phosphate, however, usually has a high specific gravity of 1.5 or larger and therefore, is easily precipitated in water. In addition, the hydroxyapatite, in spite of being fine particles (primary particles of 0.1 μm or smaller), is easily aggregated through van der Waals' force, ionic charge, or the like and therefore usually tends to form an aggregate having a particle diameter on the order of 4 to 100 μm. Since such an aggregate is significantly low dispersible in water, slurry has poor storage stability and is disadvantageously separated into water and a precipitate (hydroxyapatite aggregate) in a short time.

Thus, methods for enhancing the dispersibility of hydroxyapatite and suppressing its sedimentation (patent documents 5 to 8) have been studied as to oral compositions. Also, methods for improving the dispersibility of an insoluble substance such as an abrasive contained in mouthwashes or the like and suppressing its sedimentation (patent documents 9 and 10) are known. As for liquid food compositions, there have been proposed, for example: a food excellent in dispersion stability containing water-insoluble mineral and enzymatically degraded lecithin (patent document 11); a method for preventing calcium from being sedimented and preventing the flavor and quality of a liquid food product from being deteriorated, comprising adding insoluble calcium, lecithin, and polyglycerin fatty acid ester to the liquid food product (patent document 12); and a food composition, such as calcium-fortified milk, which is excellent both in particle homogeneity and dispersibility and in thermal stability, rarely causes sedimentation, and has favorable flavor by virtue of fine particles of calcium phosphate (patent document 13).

These proposed methods, however, still fail to offer favorable dispersion stability of calcium phosphate and cannot always produce sufficient oral compositions such as mouthwashes, liquid dentifrices, and oral detergents or liquid food compositions such as milk, soy milk, yoghurt, and refreshing beverages in which the calcium phosphate is not sedimented for a long period. Thus, an effective method has been demanded.

PRIOR ART DOCUMENTS

Patent Documents

Patent Document 1: Japanese unexamined Patent Application Publication No. 9-202717
Patent Document 2: Japanese unexamined Patent Application Publication No. 2007-308422
Patent Document 3: Japanese unexamined Patent Application Publication No. 2005-330269
Patent Document 4: WO2009/091052
Patent Document 5: Japanese unexamined Patent Application Publication No. 2008-255305
Patent Document 6: Japanese unexamined Patent Application Publication No. 2007-76995
Patent Document 7: Japanese unexamined Patent Application Publication No. 2006-246900
Patent Document 8: Japanese unexamined Patent Application Publication No. 2006-82985
Patent Document 9: Japanese unexamined Patent Application Publication No. 8-337518
Patent Document 10: Japanese unexamined Patent Application Publication No. 2001-31542
Patent Document 11: WO1998/014072

Patent Document 12: Japanese unexamined Patent Application Publication No. 9-238645
Patent Document 13: WO2004/054925

SUMMARY OF THE INVENTION

Object to be Solved by the Invention

The present invention has been made in order to solve the problems mentioned above, and an object of the present invention is to provide a liquid oral composition and a liquid food composition in which calcium phosphate such as hydroxyapatite or tricalcium phosphate can be stably dispersed and prevented from being precipitated or separated out even in long-term storage.

Means to Solve the Object

As a result of conducting diligent studies to attain the object, the present inventors have found that calcium phosphate mixed with xanthan gum and polyglycerin fatty acid ester can be stably dispersed even in long-term storage and prevented from being precipitated or separated out even when used in liquid oral compositions such as mouthwashes, liquid dentifrices, and oral detergents or in liquid food compositions such as milk, soy milk, yoghurt, and refreshing beverages. The present inventors have further found that calcium phosphate mixed with xanthan gum and polyglycerin fatty acid ester further supplemented with an amphoteric surfactant can be more effectively prevented from being precipitated or separated out in liquid oral compositions such as mouthwashes, liquid dentifrices, and oral detergents. On the basis of these findings, the present invention has been completed.

Specifically, the present invention relates to: (1) a calcium phosphate dispersion composition comprising calcium phosphate, xanthan gum, and polyglycerin fatty acid ester; (2) the calcium phosphate dispersion composition according to (1), wherein a content of the calcium phosphate is 0.01 to 20.0% by weight with respect to the total composition, a content of the xanthan gum is 0.1 to 2.0% by weight with respect to the total composition, and a content of the polyglycerin fatty acid ester is 0.01 to 2.5% by weight with respect to the total composition; (3) the calcium phosphate dispersion composition according to (1) or (2), wherein the calcium phosphate dispersion composition is obtained by adding the calcium phosphate into a solution in which the polyglycerin fatty acid ester is dissolved in an aqueous solvent, stirring the mixture, then adding the xanthan gum thereto, and stirring the mixture; (4) the calcium phosphate dispersion composition according to (1) or (2), further comprising an amphoteric surfactant; (5) the calcium phosphate dispersion composition according to (4), wherein the calcium phosphate dispersion composition is obtained by adding the calcium phosphate and the amphoteric surfactant into a solution in which the polyglycerin fatty acid ester is dissolved in an aqueous solvent, stirring the mixture, then adding the xanthan gum thereto, and stirring the mixture; (6) the calcium phosphate dispersion composition according to (4) or (5), wherein a content of the amphoteric surfactant is 0.01% by weight to 0.15% by weight with respect to the total composition; (7) the calcium phosphate dispersion composition according to any one of (4) to (6), wherein the amphoteric surfactant is alkyldiaminoethylglycine hydrochloride; (8) the calcium phosphate dispersion composition according to any one of (1) to (7), wherein the calcium phosphate is hydroxyapatite; (9) the calcium phosphate dispersion composition according to any one of (1) to (7), wherein the calcium phosphate is tricalcium phosphate; and (10) the calcium phosphate dispersion composition according to any one of (1) to (9), wherein the calcium phosphate has a particle diameter of 0.001 µm to 10 µm.

The present invention also relates to: (11) a liquid oral formulation consisting of a calcium phosphate dispersion composition according to any one of (1) to (10); (12) the liquid oral formulation according to (11), wherein the liquid oral formulation is a mouthwash, a liquid dentifrice, or an oral detergent; (13) a liquid food product consisting of a calcium phosphate dispersion composition according to (1), (2), (3), (8), (9), or (10); and (14) the liquid food product according to (13), wherein the liquid food product is a beverage, a fluid diet, or a nutrient solution.

Effect of the Invention

The present invention can provide a calcium phosphate dispersion composition that has the excellent effect of being capable of maintaining the long-term stable suspension of calcium phosphate such as hydroxyapatite in a solution without causing the precipitation of the calcium phosphate, particularly, a composition that has the effects of promoting the remineralization of teeth and of whitening teeth on liquid oral compositions and a calcium-fortified composition that enhances rich texture during drinking and consumers' preferences for liquid food compositions.

MODE OF CARRYING OUT THE INVENTION

The calcium phosphate dispersion composition of the present invention is not particularly limited as long as the composition comprises calcium phosphate, xanthan gum, and polyglycerin fatty acid ester and is capable of maintaining the long-term stable suspension of the calcium phosphate in a solution without causing the precipitation of the calcium phosphate. The calcium phosphate dispersion composition of the present invention can be used as a liquid oral formulation or a liquid food product. The content of the calcium phosphate is preferably 0.01 to 20.0% by weight, more preferably 0.1 to 5.0% by weight, with respect to the total weight of the composition. The content of the xanthan gum is preferably 0.1 to 2.0% by weight, more preferably 0.4 to 1.5% by weight, with respect to the total weight of the composition. The content of the polyglycerin fatty acid ester is preferably 0.01 to 2.5% by weight, more preferably 0.1 to 1.0% by weight, with respect to the total weight of the composition. Calcium phosphate having a smaller particle diameter is more preferred because the calcium phosphate is more easily dispersed in a liquid composition and can be prevented from being precipitated or separated out. For example, fine calcium phosphate particles having a particle diameter in the range of 0.1 to 10.0 µm are preferably used.

In addition to the above composition, the calcium phosphate dispersion composition of the present invention further comprising an amphoteric surfactant is preferred because fine calcium phosphate particles can be stably dispersed and prevented from being precipitated or separated out in a liquid oral composition even in longer-term storage. The content of the amphoteric surfactant is 0.01 to 0.15% by weight, preferably 0.05 to 0.1% by weight, with respect to the total weight of the composition.

The calcium phosphate used in the present invention is particularly desirably any of hydroxyapatite or tricalcium phosphate. The hydroxyapatite used in the present invention is one type of calcium phosphate and is synthesized by an ordinary method or is obtained from fish bone of food fish (e.g., salmon), pig bone, beef bone, or the like as a natural hard tissue. Typically, the hydroxyapatite is stoichiometrically represented by composition consisting of $Ca_{10}(PO_4)_6(OH)_2$. Alternatively, even non-stoichiometric composition where the Ca/P molar ratio is not 1.67 exhibits the properties of hydroxyapatite and can take an apatite structure. Such synthetic hydroxyapatite having, for example, a Ca/P molar ratio on the order of 1.4 to 1.8 is also included in the hydroxyapatite according to the present invention.

The tricalcium phosphate used in the present invention is preferably subject to the regulations described in the Japanese Standards of Food Additives. Preferred examples thereof can include one comprising 98.0 to 103.0% of tricalcium phosphate $[Ca_3(PO_4)_2]$ when dried. Such tricalcium phosphate is added as an anticaking agent to highly hygroscopic processed foods, for example, instant coffee, powdery dairy products, seasonings, or powdery preparations and also added as a mineral source to sports drinks or the like.

The xanthan gum used in the present invention is one type of microbial polysaccharide prepared by microbe Xanthomonas campestris-mediated fermentation from carbohydrates such as starch, glucose, or sucrose. The xanthan gum has a structure consisting principally of sodium, potassium, and calcium salts of D-glucose, D-mannose, and D-glucuronic acid and has a backbone consisting of the β-1,4 bond of D-glucose. For example, a commercially available product such as KELZAN manufactured by Sansho Co., Ltd., ECHO GUM manufactured by Dainippon Sumitomo Pharma Co., Ltd., or MONAT GUM DA, KELZAN T, and KELDENT manufactured by CP Kelco Corp. can be used as such xanthan gum.

The polyglycerin fatty acid ester used in the present invention is polyglycerin (polymerization product of glycerin) ester-bonded to fatty acid. Various polyglycerin fatty acid esters having an average degree of glycerin polymerization of 2 to 10 are commercially available. The polyglycerin fatty acid ester is found with many types depending on the degree of glycerin polymerization, the type of fatty acid, and the degree of esterification thereof and is commercially available from, for example, Sakamoto Yakuhin Kogyo Co., Ltd., Taiyo Kagaku Co., Ltd., and Kyowa Hakko Kirin Co., Ltd. Specific examples thereof can include hexaglyceryl monolaurate, hexaglyceryl monoisostearate, hexaglyceryl monomyristate, hexaglyceryl dioleate, hexaglyceryl dimyristate, hexaglyceryl dipalmitate, hexaglyceryl distearate, hexaglyceryl dibehenate, hexaglyceryl trilaurate, hexaglyceryl trimyristate, hexaglyceryl tripalmitate, hexaglyceryl tristearate, hexaglyceryl tribehenate, hexaglyceryl tetralaurate, hexaglyceryl tetramyristate, hexaglyceryl tetrapalmitate, hexaglyceryl tetrastearate, hexaglyceryl tetrabehenate, hexaglyceryl pentalaurate, hexaglyceryl pentamyristate, hexaglyceryl pentapalmitate, hexaglyceryl pentastearate, hexaglyceryl pentabehenate, decaglyceryl monocaprate, decaglyceryl monolaurate, decaglyceryl monomyristate, decaglyceryl monopalmitate, decaglyceryl monostearate, decaglyceryl monooleate, decaglyceryl monolinoleate, decaglyceryl monoisostearate, decaglyceryl dicaprate, decaglyceryl dilaurate, decaglyceryl dimyristate, decaglyceryl dipalmitate, decaglyceryl distearate, decaglyceryl diisostearate, decaglyceryl trilaurate, decaglyceryl trimyristate, decaglyceryl tripalmitate, decaglyceryl tristearate, decaglyceryl trioleate, decaglyceryl tribehenate, decaglyceryl pentastearate, decaglyceryl pentaoleate, decaglyceryl pentaisostearate, decaglyceryl heptastearate, decaglyceryl decastearate, decaglyceryl decaoleate, and decaglyceryl decaisostearate. These polyglycerin fatty acid esters may be used alone or may be used in arbitrary combination of two or more thereof.

Examples of the amphoteric surfactant used in the present invention include, but not particularly limited to, amino acid-type and betaine-type amphoteric surfactants. Among them, amino acid-type amphoteric surfactants are preferably used. Of these amino acid-type amphoteric surfactants, alkyldiaminoethylglycine hydrochloride is particularly preferably used. The alkyldiaminoethylglycine hydrochloride can be purchased from, for example, Alfresa Pharma Corp., Yoshida Pharmaceutical Co., Ltd., Nichi-Iko Pharmaceutical Co., Ltd., and Iwaki Seiyaku Co., Ltd.

The liquid oral formulation (liquid oral composition) of the present invention comprises, as its components, the calcium phosphate, the xanthan gum, and the polyglycerin fatty acid ester, and, preferably, the amphoteric surfactant and further comprises water. The liquid oral formulation (liquid oral composition) of the present invention may further comprise additives such as a wetting agent, a flavoring agent, a sweetener, an antiseptic, a solubilizer, a pH adjuster, a thickener, an additional surfactant other than those described above, a crude drug extract, an additional medical component, and a germicide.

Examples of the wetting agent include polyhydric alcohols such as polyethylene glycol, propylene glycol, sorbitol, glycerin, maltitol, xylitol, and erythritol.

Examples of the flavoring agent include: natural flavors such as spearmint oil, peppermint oil, wintergreen oil, sassafras oil, clove oil, sage oil, eucalyptus oil, thyme oil, anise oil, rosemary oil, cinnamon oil, perilla oil, lemon oil, and orange oil; and synthetic flavors such as 1-menthol, thymol, anethole, carvone, eugenol, methyl salicylate, limonene, ocimene, methyl acetate, citronellyl acetate, citronellol, cineol, vanillin, linalool, ethyl linalool, and thymol methyl salicylate.

Examples of the sweetener include saccharin, saccharin sodium, stevioside, and aspartame. Examples of the antiseptic include benzoic acid, sodium benzoate, and p-hydroxybenzoate esters.

The solubilizer is used as a stabilizer for oily substances. Preferred examples of the solubilizer include sodium alkyl sulfate, alkyl phosphate, sodium alkylbenzenesulfonate, alkyl phosphate, sodium alkylbenzenesulfonate, sodium N-acyl sarcosinate, N-acyl glutamate, polyoxyethylene hydrogenated castor oil, polyoxyethylene-polyoxypropylene copolymers, polyoxyethylene-polyoxypropylene fatty acid ester, sucrose fatty acid ester, sugar alcohol fatty acid ester, alkyl glycosides, sorbitan fatty acid ester, polyoxyethylene sorbitan fatty acid ester, alkyldimethylamine oxide, and alkyl betaines.

Examples of the pH adjuster include components having buffering ability, such as citric acid and salts thereof, phosphoric acid and salts thereof, tartaric acid, ascorbic acid, malic acid, fumaric acid, succinic acid, malonic acid, lactic acid, sodium borate, sodium carbonate, sodium bicarbonate, potassium carbonate, potassium bicarbonate, ammonium carbonate, and sodium sesquicarbonate.

Examples of the thickener include: cellulose derivatives such as carboxymethylcellulose and carboxymethylcellulose sodium; alkali metal alginates such as sodium alginate; gums such as gum arabic; synthetic binders such as sodium polyacrylate and polyvinylpyrrolidone; natural polymers such as carrageenan; and inorganic binders such as silica gel and Laponite.

Examples of the additional surfactant include anionic surfactants including: fatty acid salts such as sodium laurate; higher alkyl sulfuric acid ester salts such as sodium lauryl sulfate; alkyl ether sulfuric acid ester salts such as POE-triethanolamine lauryl sulfate; and N-acyl sarcosinate, sulfosuccinate, and N-acylamino acid salts, also include cationic surfactants including: alkyl trimethylammonium salts such as stearyl trimethyl ammonium chloride; and benzalkonium chloride and benzethonium chloride, and further include nonionic surfactants including: sorbitan fatty acid esters such as sorbitan monooleate; and hydrogenated castor oil derivatives.

Examples of the crude drug extract include extracts of arnica, aloe, ginkgo, oolong tea, anise, *Hypericum erectum*, *Phellodendron amurense*, matricaria, chamomilla, licorice roots, *Sasa veitchii*, gardenia, cinnamon, black tea, *Lithospermum* roots, white birch, sage, *Camellia sinensis*, clove, *Angelica acutiloba*, carrot, eglantine, *Hamamelis*, loquat leaves, grape seeds, soapberry, rosemary, rose hips, Saint John's wort, etc.

Examples of the additional medical component and the germicide include sodium copper chlorophyllin, sodium iron chlorophyllin, isopropylmethylphenol, hinokitiol, cetylpyridinium chloride, benzalkonium chloride, benzethonium chloride, dequalinium chloride, pyridoxine hydrochloride, chlorhexidines, triclosan, azulene, azulene sulfonate, allantoin, aluminum chlorohydroxy allantoinate, epidihydrocholesterin glycyrrhizinic acid and salts thereof, glycyrrhetinic acid, epsilon-aminocaproic acid, dextranase, mutanase, lysozyme, amylase, protease, lytic enzymes, sodium monofluorophosphate, potassium monofluorophosphate, sodium fluoride, tocopherols, potassium nitrate, aluminum lactate, and sodium chloride.

The liquid food composition of the present invention comprises, as its components, the calcium phosphate, the xanthan gum, and the polyglycerin fatty acid ester and may further comprise, if necessary, various appropriate components generally used in ordinary foods, such as an edulcorant, an acidulant, a thickener, an emulsifier, a pH adjuster, an organic acid, a colorant, a flavor, a seasoning, a preservative, vitamins, minerals, and a medicinal component, without impairing the effects of the present invention.

Examples of the edulcorant include saccharose (sugar), fructose, maltitol, glucose, various oligosaccharides, starch syrup, reduced malt sugar starch syrup, maltotriose, honey, palatinose, trehalose, lactose, xylose, aspartame, sucrose, L-phenylalanine, stevia, saccharin, acesulfame-potassium, licorice roots, stevioside, rebaudioside, sugar alcohols such as sorbitol, mannitol, xylitol, erythritol, lactitol, and maltitol, and oligosaccharides such as fructooligosaccharide, galactooligosaccharide, milk oligosaccharide, and xylooligosaccharide.

Examples of the acidulant include: food organic acids such as citric acid, lactic acid, malic acid, tartaric acid, succinic acid, and gluconic acid; and salts such as sodium salt, calcium salt, and potassium salt.

Examples of the thickener include ghatti gum, pullulan, gum arabic, soybean polysaccharides, tamarind seed gum, pectin, carrageenan, processed *Eucheuma* seaweed, agar, furcellaran, alginic acids (alginic acid and alginate), guar gum, Tara gum, locust bean gum, psyllium seed gum, xanthan gum, *Artemisia sphaerocephala* seed gum, glucomannan, quince seeds, starch, modified starch, processed starch, dextrin, deacylated gellan gum, native gellan gum, curdlan, rhamsan gum, welan gum, Macrophomopsis gum, tragacanth gum, karaya gum, microcrystalline cellulose, cellulose microfibers, fermented cellulose, carboxymethylcellulose salt, methylcellulose, hydroxypropylcellulose, hydroxymethylcellulose, chitin, chitosan, casein, dextrin, gelatin, other polysaccharides, and starches derived from plants such as potato, sweet potato, corn, tapioca, rice, wheat, kudzu, and bracken.

The emulsifier is not particularly limited as long as the emulsifier is an edible one. Examples thereof include sucrose fatty acid ester, glycerin fatty acid ester (e.g., polyglycerin fatty acid ester and monoglycerin fatty acid ester), propylene glycol fatty acid ester, sorbitan fatty acid ester, phospholipid (e.g., lecithin, lysolecithin, and lipoprotein), sodium stearoyl lactate, and enzymatically degraded phospholipid (e.g., enzymatically degraded lecithin).

A wide range of naturally occurring organic acids or alkalis or organic acids or alkalis obtained by a microbial fermentation method or chemical synthesis, which are usually used in foods, can be used as the pH adjuster. The pH adjuster also includes the acidulant, etc. mentioned above. Examples thereof include itaconic acid, α-ketoglutaric acid, phytic acid, mevalonic acid, adipic acid, citric acid, gluconic acid, succinic acid, glacial acetic acid, tartaric acid, lactic acid, hydrochloric acid, acetic acid, fumaric acid, malic acid, phosphoric acid, acidic pyrophosphoric acid, and their sodium salts, potassium salts, calcium salts, ammonium salts, and calcium carbonate, calcium hydroxide, calcium phosphate, monosodium phosphate, disodium phosphate, trisodium phosphate, sodium pyrophosphate, sodium polyphosphate, sodium tripolyphosphate, potassium pyrophosphate, sodium hexametaphosphate, sodium metaphosphate, potassium metaphosphate, monosodium fumarate, sodium bicarbonate, sodium carbonate, potassium bicarbonate, potassium carbonate, ammonium bicarbonate, potassium hydroxide, and sodium hydroxide.

Examples of the organic acids include: organic acids such as citric acid, isocitric acid, malic acid, acetic acid, oxalic acid, malonic acid, succinic acid, glutaric acid, maleic acid, fumaric acid, aconitic acid, lactic acid, tartaric acid, pyruvic acid, ascorbic acid, aldonic acid, and uronic acid; and ume plum vinegar, apple vinegar, citrus (e.g., lemon, orange,

*Citrus junos*, and *Citrus natsudaidai*) chips, powders, and extracts containing these organic acids.

Examples of the colorant include coffee powders, cacao pigment, lac color, red cabbage pigment, red radish pigment, *Clitoria ternatea* pigment, perilla pigment, hibiscus pigment, grape juice color, grape skin pigment, purple sweet potato color, purple corn color, purple yam color, elderberry pigment, cranberry pigment, cherry pigment, hibiscus pigment, blackberry pigment, plum pigment, blueberry pigment, raspberry pigment, boysenberry pigment, tomato pigment, lac color, strawberry pigment, cacao pigment, caramel color, gardenia pigment, Monascus color, cochineal pigment, red beet pigment, grape juice color, safflower pigment, annatto pigment, gardenia yellow pigment, turmeric pigment, Gardenia Yellow, amaranth (Food Red No. 2), erythrosine (Food Red No. 3), Allura Red AC (Food Red No. 40), New Coccine (Food Red No. 102), phloxine (Food Red No. 104), rose bengal (Food Red No. 105), acid red (Food Red No. 106), brilliant blue (Food Blue No. 1), indigocarmine (Food Blue No. 2), spirulina pigment, and gardenia pigment.

The flavor consists of one or a mixture of two or more selected from among, for example, natural flavor ingredients such as essential oils, extracts, oleoresin, recovery flavors, and isolated flavors, and synthetic flavor ingredients such as alcohols, esters, aldehydes, ketones, and lactones. Examples of its form can include flavoring agents such as aqueous flavors, oil flavors, emulsified flavors, and powder flavors. Specific examples thereof include: natural flavors such as lemon oil, orange oil, anise oil, clove oil, capsicum oil, cinnamon oil, grapefruit oil, lime oil, tangerine oil, mandarin oil, bergamot oil, peppermint oil, and spearmint oil; alcohols such as linalool, geraniol, citronellol, myrcenol, farnesol, hexanol, benzyl alcohol, phenylethyl alcohol, anise alcohol, cinnamic alcohol, anethole, linalool, and eugenol; esters such as ethyl acetate, butyl acetate, citronellyl acetate, benzyl acetate, linalyl acetate, ethyl propionate, isoamyl propionate, geranyl propionate, isoamyl butyrate, and ethyl isovalerate; aldehydes and ketones such as octyl aldehyde, undecyl aldehyde, α-hexyl cinnamaldehyde, nonadienal, octanal, citral, perillaldehyde, phenyl aldehyde, cinnamic aldehyde, vanillin, L-carvone, acetophenone, ionone, damascenone, maltol, benzyl acetone, methyl heptyl ketone, and methyl decyl ketone; lactones such as δ-decalactone, γ-undecalactone, and sclareolide; hydrocarbons such as limonene, pinene, and caryophyllene; and acids such as acetic acid, propionic acid, 2-methylbutyric acid, and cinnamic acid.

Examples of the seasoning include common salt, sodium glutamate, inosinic acid, and guanylic acid.

Examples of the preservative include sorbic acid and salts thereof, benzoic acid and salts thereof, dehydroacetic acid and salts thereof, p-hydroxybenzoate esters, propionic acid and salts thereof, sodium acetate, sodium sulfite, sodium hyposulfite, sulfur dioxide, ethanol, glycine, polylysine, protamine, lysozyme, chitosan, pectin degradation products, extracts of plants such as yucca, mustard, wasabi, hop, and mousou bamboo, hinokitiol, natamycin, nisin, chlorine germicides such as sodium hypochlorite and high test bleaching powder, and oxygen germicides such as hydrogen peroxide.

Examples of the vitamins include vitamin C, vitamin D, vitamin E, vitamin A, and vitamin B12.

Examples of the minerals include calcium, magnesium, iron, zinc, and copper.

Examples of the medicinal component include squeezed juice of aloe, *Gynostemma pentaphyllum*, ginseng, active oxygen scavengers, antioxidants, anti-inflammatory analgesics, antihistaminic agents, antipruritics, germicides, vitamins, and hormones.

EXAMPLES

Hereinafter, the present invention will be described specifically with reference to Examples and Comparative Examples. However, the present invention is not intended to be limited by Examples below. In Examples, etc., the polyglycerin fatty acid ester used was "SUNSOFT A-181E-C" manufactured by Taiyo Kagaku Co., Ltd.; the xanthan gum used was "KELTROL CG-SFT" manufactured by Sansho Co., Ltd.; the alkyldiaminoethylglycine hydrochloride used was "TEGO 51 (10%)" manufactured by Alfresa Pharma Corp.; and the glycerin used was "Japanese Pharmacopoeia Concentrated Glycerin" manufactured by Kao Corp.

[Hydroxyapatite]

Hydroxyapatite was produced by adding 168 g of 85% phosphoric acid diluted with 200 g of water into a suspension of calcium hydroxide (200 g) in 1.5 L of water and preparing a hydroxyapatite suspension according to a routine method. The particle diameter of fine hydroxyapatite particles in the suspension was measured using a laser diffraction/scattering particle size distribution analyzer (manufactured by HORIBA, Ltd.). The obtained hydroxyapatite had a particle diameter of 0.1 to 10 μm and a median diameter of 2 to 3 μm.

[Tricalcium Phosphate (TCP)]

β-TCP manufactured by Taihei Chemical Industrial Co., Ltd. was used and had a particle diameter of 0.1 to 10 μm and a median diameter of 6 μm. Its particle diameter was measured using a laser diffraction/scattering particle size distribution analyzer (manufactured by HORIBA, Ltd.), as in the measurement of the fine hydroxyapatite particles.

<<Liquid Oral Composition>>

[Mouthwash]

Hydroxyapatite was added at a final concentration of 0.01% to an aqueous solution containing 2.5% (final concentration) of polyglycerin fatty acid ester, and the mixture was stirred at 7000 rpm for 5 minutes. Then, xanthan gum dispersed in advance in glycerin was added thereto at a final concentration of 2.0%, and the mixture was further stirred for 10 minutes to obtain a mouthwash of Example 1. Also, mouthwashes of Examples 2 to 12 and Comparative Examples 1 to 4 were obtained in the same way as in Example 1 except that the contents of polyglycerin fatty acid ester, hydroxyapatite, and xanthan gum were changed as described in Tables 1 to 3.

Tricalcium phosphate was added at a final concentration of 0.01% to an aqueous solution containing 2.5% (final concentration) of polyglycerin fatty acid ester, and the mixture was stirred at 7000 rpm for 5 minutes. Then, xanthan gum dispersed in advance in glycerin was added thereto at a final concentration of 2.0%, and the mixture was further stirred for 10 minutes to obtain a mouthwash of Example 13. Also, mouthwashes of Examples 14 and 16 to 22 and Comparative Examples 5 to 8 were obtained in the same way as in Example 13 except that the contents of polyglycerin fatty acid ester, tricalcium phosphate, and xanthan gum were changed as described in Tables 4 to 6.

Tricalcium phosphate and hydroxyapatite were added at final concentrations of 8.0% and 2.0%, respectively, to an aqueous solution containing 0.1% (final concentration) of polyglycerin fatty acid ester, and the mixture was stirred at 7000 rpm for 10 minutes. Then, xanthan gum dispersed in advance in glycerin was added thereto at a final concentration of 0.4%, and the mixture was further stirred for 10 minutes to obtain a mouthwash of Example 15.

[Liquid Dentifrice]

Hydroxyapatite was added at a final concentration of 2.0% to an aqueous solution containing 1.0% (final concentration) of polyglycerin fatty acid ester, and the mixture was stirred at 7000 rpm for 5 minutes. Then, xanthan gum dispersed in advance in glycerin was added thereto at a final concentration of 0.5%, and the mixture was further stirred for 10 minutes to obtain a liquid dentifrice of Example 23. Also, liquid dentifrices of Examples 24 to 26 and Comparative Examples 9 and 10 were obtained in the same way as in Example 23 except that the contents of polyglycerin fatty acid ester, hydroxyapatite, and xanthan gum were changed as described in Table 7.

[Oral Detergent]

Hydroxyapatite was added at a final concentration of 0.5% to an aqueous solution containing 0.05% (final concentration) of polyglycerin fatty acid ester, and the mixture was stirred at 7000 rpm for 5 minutes. Then, xanthan gum dispersed in advance in glycerin was added thereto at a final concentration of 0.1%, and the mixture was further stirred for 10 minutes to obtain an oral detergent of Example 27. Also, oral detergents of Examples 28 to 30 and Comparative Example 11 were obtained in the same way as in Example 27 except that the contents of polyglycerin fatty acid ester, hydroxyapatite, and xanthan gum were changed as described in Table 8.

<<Liquid Food Composition>>

[Beverage]

Hydroxyapatite was added at a final concentration of 0.01% to an aqueous solution containing 2.5% (final concentration) of polyglycerin fatty acid ester and 0.05% (final concentration) of sodium benzoate, and the mixture was stirred at 7000 rpm for 5 minutes. Then, xanthan gum was added thereto at a final concentration of 2.0%, and the mixture was further stirred for 20 minutes to obtain a beverage of Example 31. Also, beverages of Examples 32, 33, 36, 38, 40, and 41 and Comparative Examples 12 and 13 were obtained in the same way as in Example 31 except that the contents of polyglycerin fatty acid ester, hydroxyapatite, and xanthan gum were changed as described in Tables 9 to 11.

Hydroxyapatite and tricalcium phosphate were added at final concentrations of 5.0% and 5.0%, respectively, to an aqueous solution containing 0.1% (final concentration) of polyglycerin fatty acid ester and 0.05% (final concentration) of sodium benzoate, and the mixture was stirred at 7000 rpm for 5 minutes. Then, xanthan gum was added thereto at a final concentration of 0.4%, and the mixture was further stirred for 20 minutes to obtain a beverage of Example 34. Also, beverages of Examples 35, 37, and 39 and Comparative Example 14 were obtained in the same way as in Example 34 except that the contents of polyglycerin fatty acid ester, hydroxyapatite, and xanthan gum were changed as described in Tables 9 to 11.

[Soup]

Hydroxyapatite was added at a final concentration of 1.0% to an aqueous solution containing 0.5% (final concentration) of polyglycerin fatty acid ester, and the mixture was stirred at 7000 rpm for 5 minutes. Then, xanthan gum was added thereto at a final concentration of 1.0%, and the mixture was further stirred for 10 minutes to obtain a soup of Example 42. Also, soups of Example 43 and Comparative Examples 15 and 16 were obtained in the same way as in Example 42 except that the contents of polyglycerin fatty acid ester, hydroxyapatite, and xanthan gum were changed as described in Table 12.

[Nutrient Solution]

Tricalcium phosphate was added at a final concentration of 20.0% to soy milk containing 1.0% (final concentration) of polyglycerin fatty acid ester, and the mixture was stirred at 7000 rpm for 5 minutes. Then, xanthan gum was added thereto at a final concentration of 2.0%, and the mixture was further stirred for 10 minutes to obtain a nutrient solution of Example 44. Also, nutrient solutions of Examples 45 to 47 and Comparative Examples 17 to 19 were obtained in the same way as in Example 44 except that the contents of polyglycerin fatty acid ester, tricalcium phosphate, and xanthan gum were changed as described in Table 13.

Components to be contained, such as a flavor and sorbitol, other than the components described in the production methods of the above Examples and Comparative Examples were added after each described production method.

Various preparations of the above Examples and Comparative Examples were subjected to viscosity measurement and evaluation tests for their dispersion stability, redispersibility, and usability by evaluation methods described below. The results about [Mouthwash] are shown in Tables 1 to 6. The results about [Liquid dentifrice] are shown in Table 7. The results about [Oral detergent] are shown in Table 8. The results about [Beverage] are shown in Tables 9 to 11. The results about [Soup] are shown in Table 12. The results about [Nutrient solution] are shown in Table 13. The viscosity serves as an index for usability and means that a viscosity of approximately 6000 (mPa·s) or higher reduces flowability and makes the product difficult to remove from a container. In this context, the viscosity was measured using a type B viscometer.

[Dispersion Stability]

This test was carried out at a temperature of 25° C. at a rotational speed of 2000 rpm for a rotation time of minutes using a centrifuge. The degree of dispersibility was determined by visual evaluation. The evaluation was made at four scales: Excellent, Good, Fair, and Poor.

Excellent: No precipitation found.

Good: Approximately 1/6 precipitated (whitish liquid/white precipitates).

Fair: Approximately 1/3 precipitated (whitish liquid/white precipitates).

Poor: Completely precipitated (transparent or semitransparent supernatant).

[Redispersibility]

After centrifugation, each sample was shaken again. The degree of dispersibility was determined by visual observation according to Excellent, Good, Fair, and Poor.

Excellent: No need to be shaken.

Good: Redispersed by slight shaking.

Fair: Dispersible by vigorous shaking.

Poor: Not redispersed even by shaking.

[Usability]

The flowability was observed according to the state or manner of ejection from a container.

Good: A mouthwash (or a drink) had favorable flowability.

Fair: A mouthwash (or a drink) had low flowability, but was able to be used.

Poor: A mouthwash (or a drink) had inappropriate flowability.

TABLE 1

| | Example No. | | | | | |
|---|---|---|---|---|---|---|
| | 1 | 2 | 3 | 4 | 5 | 6 |
| Hydroxyapatite | 0.01 | 1.0 | 5.0 | 10.0 | 20.0 | 0.01 |
| Xanthan gum | 2.0 | 1.5 | 0.7 | 0.4 | 0.1 | 2.0 |
| Polyglycerin fatty acid ester | 2.5 | 1.0 | 0.25 | 0.1 | 0.01 | 2.5 |
| Alkyldiaminoethylglycine hydrochloride | 0.0 | 0.0 | 0.0 | 0.0 | 0.0 | 0.15 |
| Glycerin | 10.0 | 10.0 | 10.0 | 10.0 | 10.0 | 10.0 |
| Flavor | 0.3 | 0.3 | 0.3 | 0.3 | 0.3 | 0.3 |
| Water | Balance | Balance | Balance | Balance | Balance | Balance |
| Viscosity (mPa·s) | 4510 | 3480 | 1460 | 1472 | 1413 | 4730 |
| Dispersion stability evaluation | Good | Excellent | Excellent | Excellent | Good | Excellent |
| Redispersibility evaluation | Good | Excellent | Excellent | Excellent | Good | Excellent |
| Usability | Good | Good | Good | Good | Good | Good |

TABLE 2

| | Example No. | | | | | |
|---|---|---|---|---|---|---|
| | 7 | 8 | 9 | 10 | 11 | 12 |
| Hydroxyapatite | 20.0 | 1.0 | 10.0 | 10.0 | 1.0 | 25.0 |
| Xanthan gum | 0.1 | 0.05 | 2.5 | 0.4 | 1.5 | 1.5 |
| Polyglycerin fatty acid ester | 0.01 | 1.0 | 0.1 | 0.005 | 3.0 | 1.0 |
| Alkyldiaminoethylglycine hydrochloride | 0.01 | 0.0 | 0.1 | 0.1 | 0.0 | 0.1 |
| Glycerin | 10.0 | 10.0 | 10.0 | 10.0 | 10.0 | 10.0 |
| Flavor | 0.3 | 0.3 | 0.3 | 0.3 | 0.3 | 0.3 |
| Water | Balance | Balance | Balance | Balance | Balance | Balance |
| Viscosity (mPa·s) | 1465 | ≤30 | 6470 | 1540 | 2210 | 6145 |
| Dispersion stability evaluation | Excellent | Fair | Good | Good | Good | Good |
| Redispersibility evaluation | Excellent | Fair | Good | Good | Fair | Fair |
| Usability | Good | Good | Good | Good | Good | Fair |

TABLE 3

| | Comparative Example No. | | | |
|---|---|---|---|---|
| | 1 | 2 | 3 | 4 |
| Hydroxyapatite | 1.0 | 10.0 | 10.0 | 1.0 |
| Xanthan gum | 0.0 | 1.0 | 0.0 | 0.0 |
| Polyglycerin fatty acid ester | 0.0 | 0.0 | 1.0 | 0.0 |
| Alkyldiaminoethylglycine hydrochloride | 0.0 | 0.1 | 0.1 | 0.1 |
| Glycerin | 10.0 | 10.0 | 10.0 | 10.0 |
| Flavor | 0.3 | 0.3 | 0.3 | 0.3 |
| Water | Balance | Balance | Balance | Balance |
| Viscosity (mPa·s) | ≤30 | 2890 | 1320 | ≤30 |
| Dispersion stability evaluation | Poor | Fair | Poor | Poor |
| Redispersibility evaluation | Poor | Poor | Poor | Poor |
| Usability | Good | Good | Good | Good |

TABLE 4

| | Example No. | | | | |
|---|---|---|---|---|---|
| | 13 | 14 | 15 | 16 | 17 |
| Hydroxyapatite | 0.0 | 0.0 | 2.0 | 0.0 | 0.0 |
| Tricalcium phosphate | 0.01 | 1.0 | 8.0 | 20.0 | 1.0 |
| Xanthan gum | 2.0 | 1.5 | 0.4 | 0.1 | 1.5 |
| Polyglycerin fatty acid ester | 2.5 | 1.0 | 0.1 | 0.01 | 1.0 |
| Alkyldiaminoethylglycine hydrochloride | 0.0 | 0.0 | 0.0 | 0.0 | 0.1 |
| Glycerin | 10.0 | 10.0 | 10.0 | 10.0 | 10.0 |
| Flavor | 0.3 | 0.3 | 0.3 | 0.3 | 0.3 |
| Water | Balance | Balance | Balance | Balance | Balance |
| Viscosity (mPa·s) | 4650 | 3230 | 1110 | 1375 | 3245 |
| Dispersion stability evaluation | Good | Good | Good | Good | Excellent |
| Redispersibility evaluation | Good | Good | Good | Good | Excellent |
| Usability | Good | Good | Good | Good | Good |

TABLE 5

| | Example No. | | | | |
|---|---|---|---|---|---|
| | 18 | 19 | 20 | 21 | 22 |
| Tricalcium phosphate | 20.0 | 1.0 | 10.0 | 10.0 | 25.0 |
| Xanthan gum | 0.1 | 0.05 | 2.5 | 0.4 | 1.5 |
| Polyglycerin fatty acid ester | 0.01 | 1.0 | 0.1 | 0.005 | 1.0 |
| Alkyldiaminoethylglycine hydrochloride | 0.05 | 0.1 | 0.0 | 0.1 | 0.0 |
| Glycerin | 10.0 | 10.0 | 10.0 | 10.0 | 10.0 |
| Flavor | 0.3 | 0.3 | 0.3 | 0.3 | 0.3 |
| Water | Balance | Balance | Balance | Balance | Balance |
| Viscosity (mPa·s) | 1390 | ≤30 | 6200 | 1335 | 5970 |
| Dispersion stability evaluation | Excellent | Fair | Good | Good | Good |
| Redispersibility evaluation | Excellent | Fair | Good | Fair | Fair |
| Usability | Good | Good | Fair | Good | Fair |

TABLE 6

| | Comparative Example No. | | | |
|---|---|---|---|---|
| | 5 | 6 | 7 | 8 |
| Tricalcium phosphate | 1.0 | 10.0 | 10.0 | 1.0 |
| Xanthan gum | 0.0 | 1.0 | 0.0 | 0.0 |
| Polyglycerin fatty acid ester | 0.0 | 0.0 | 1.0 | 0.0 |
| Alkyldiaminoethylglycine hydrochloride | 0.0 | 0.1 | 0.1 | 0.1 |
| Glycerin | 10.0 | 10.0 | 10.0 | 10.0 |
| Flavor | 0.3 | 0.3 | 0.3 | 0.3 |
| Water | Balance | Balance | Balance | Balance |
| Viscosity (mPa·s) | ≤30 | 2770 | 1380 | ≤30 |
| Dispersion stability evaluation | Poor | Fair | Poor | Poor |
| Redispersibility evaluation | Poor | Poor | Poor | Poor |
| Usability | Good | Good | Good | Good |

TABLE 7

| | Example No. | | | | Comparative Example No. | |
|---|---|---|---|---|---|---|
| | 23 | 24 | 25 | 26 | 9 | 10 |
| Hydroxyapatite | 2.0 | 8.0 | 2.0 | 8.0 | 2.0 | 8.0 |
| Xanthan gum | 0.5 | 2.0 | 0.05 | 0.1 | 0.0 | 2.0 |
| Polyglycerin fatty acid ester | 1.0 | 0.05 | 1.0 | 3.0 | 1.0 | 0.0 |
| Sodium lauryl sulfate | 1.0 | 1.0 | 1.0 | 1.0 | 1.0 | 1.0 |
| Xylitol | 0.5 | 0.5 | 0.5 | 0.5 | 0.5 | 0.5 |
| Polyethylene glycol | 5.0 | 5.0 | 5.0 | 5.0 | 5.0 | 5.0 |
| Sorbitol (70%) | 40.0 | 40.0 | 40.0 | 40.0 | 40.0 | 40.0 |
| Glycerin | 10 | 10 | 10 | 10 | 10 | 10 |
| Flavor | 1.0 | 1.0 | 1.0 | 1.0 | 1.0 | 1.0 |
| Water | Balance | Balance | Balance | Balance | Balance | Balance |
| Viscosity (mPa·s) | 1650 | 5210 | ≤30 | 85 | ≤30 | 6120 |
| Dispersion stability evaluation | Excellent | Excellent | Fair | Good | Poor | Poor |
| Redispersibility evaluation | Excellent | Excellent | Fair | Fair | Poor | Poor |
| Usability | Good | Good | Good | Good | Good | Good |

TABLE 8

| | Example No. | | | | Comparative Example No. |
|---|---|---|---|---|---|
| | 27 | 28 | 29 | 30 | 11 |
| Hydroxyapatite | 0.5 | 0.5 | 0.5 | 0.5 | 0.5 |
| Xanthan gum | 0.1 | 1.0 | 0.1 | 1.0 | 1.0 |
| Polyglycerin fatty acid ester | 0.05 | 0.1 | 0.05 | 0.05 | 0.0 |
| Alkyldiaminoethylglycine hydrochloride | 0.0 | 0.0 | 0.1 | 0.0 | 0.0 |
| Dipotassium glycyrrhizinate | 1.0 | 1.0 | 1.0 | 1.0 | 1.0 |
| Glycerin | 3.0 | 3.0 | 3.0 | 3.0 | 3.0 |
| Menthol | 2.0 | 2.0 | 2.0 | 2.0 | 2.0 |
| Eucalyptus oil | 0.1 | 0.1 | 0.1 | 0.1 | 0.1 |
| Clove oil | 0.1 | 0.1 | 0.1 | 0.1 | 0.1 |
| Water | Balance | Balance | Balance | Balance | Balance |
| Viscosity (mPa·s) | 1490 | 3120 | 1590 | 4550 | 3245 |
| Dispersion stability evaluation | Excellent | Excellent | Excellent | Good | Fair |
| Redispersibility evaluation | Excellent | Excellent | Excellent | Good | Poor |
| Usability | Good | Good | Good | Good | Good |

TABLE 9

| | Example No. | | | | |
|---|---|---|---|---|---|
| | 31 | 32 | 33 | 34 | 35 |
| Hydroxyapatite | 0.01 | 1.0 | 2.5 | 5.0 | 10.0 |
| Tricalcium phosphate | 0.0 | 0.0 | 0.0 | 5.0 | 10.0 |
| Xanthan gum | 2.0 | 1.5 | 0.7 | 0.4 | 0.1 |
| Polyglycerin fatty acid ester | 2.5 | 1.0 | 0.1 | 0.1 | 0.01 |
| Sodium benzoate | 0.05 | 0.05 | 0.05 | 0.05 | 0.05 |
| Sorbitol | 13.0 | 13.0 | 13.0 | 13.0 | 13.0 |
| Flavor | 0.3 | 0.3 | 0.3 | 0.3 | 0.3 |
| Water | Balance | Balance | Balance | Balance | Balance |
| Viscosity (mPa·s) | 4700 | 3465 | 1280 | 1488 | 1405 |

TABLE 9-continued

| | Example No. | | | | |
|---|---|---|---|---|---|
| | 31 | 32 | 33 | 34 | 35 |
| Dispersion stability evaluation | Excellent | Excellent | Excellent | Excellent | Good |
| Redispersibility evaluation | Excellent | Excellent | Excellent | Excellent | Good |
| Usability | Good | Good | Good | Good | Good |

TABLE 10

| | Example No. | | | | | |
|---|---|---|---|---|---|---|
| | 36 | 37 | 38 | 39 | 40 | 41 |
| Hydroxyapatite | 20.0 | 0.5 | 10.0 | 5.0 | 1.0 | 25.0 |
| Tricalcium phosphate | 0.0 | 0.5 | 0.0 | 5.0 | 0.0 | 0.0 |
| Xanthan gum | 1.5 | 0.05 | 2.5 | 0.4 | 1.5 | 1.5 |
| Polyglycerin fatty acid ester | 1.0 | 1.0 | 0.1 | 0.005 | 3.0 | 1.0 |
| Sodium benzoate | 0.05 | 0.05 | 0.05 | 0.05 | 0.05 | 0.05 |
| Sorbitol | 13.0 | 13.0 | 13.0 | 13.0 | 13.0 | 13.0 |
| Flavor | 0.3 | 0.3 | 0.3 | 0.3 | 0.3 | 0.3 |
| Water | Balance | Balance | Balance | Balance | Balance | Balance |
| Viscosity (mPa · s) | 5930 | ≤30 | 6440 | 1512 | 2100 | 6210 |
| Dispersion stability evaluation | Good | Fair | Good | Good | Good | Good |
| Redispersibility evaluation | Good | Fair | Good | Fair | Fair | Fair |
| Usability | Fair | Good | Fair | Good | Fair | Fair |

TABLE 11

| | Comparative Example No. | | |
|---|---|---|---|
| | 12 | 13 | 14 |
| Hydroxyapatite | 1.0 | 2.5 | 5.0 |
| Tricalcium phosphate | 0.0 | 0.0 | 5.0 |
| Xanthan gum | 0.0 | 0.7 | 0.0. |
| Polyglycerin fatty acid ester | 1.0 | 0.0 | 0.0 |
| Sodium benzoate | 0.05 | 0.05 | 0.05 |
| Sorbitol | 13.0 | 13.0 | 13.0 |
| Flavor | 0.3 | 0.3 | 0.3 |
| Water | Balance | Balance | Balance |
| Viscosity (mPa · s) | ≤30 | 1412 | ≤30 |
| Dispersion stability evaluation | Poor | Poor | Poor |
| Redispersibility evaluation | Poor | Poor | Poor |
| Usability | Good | Good | Good |

TABLE 12

| | Example No. | | Comparative Example No. | |
|---|---|---|---|---|
| | 42 | 43 | 15 | 16 |
| Hydroxyapatite | 1.0 | 5.0 | 1.0 | 5.0 |
| Xanthan gum | 1.0 | 0.5 | 0.0 | 0.5 |
| Polyglycerin fatty acid ester | 0.5 | 2.0 | 0.5 | 0.0 |
| Soy milk | 20 | 20 | 20 | 20 |
| Sugar | 2 | 2 | 2 | 2 |
| Common salt | 0.5 | 0.5 | 0.5 | 0.5 |
| Water | Balance | Balance | Balance | Balance |
| Viscosity (mPa · s) | 3250 | 2010 | 42 | 1980 |
| Dispersion stability evaluation | Excellent | Excellent | Poor | Fair |
| Redispersibility evaluation | Excellent | Excellent | Poor | Poor |
| Usability | Good | Good | Good | Good |

TABLE 13

| | Example No. | | | | Comparative Example No. | | |
|---|---|---|---|---|---|---|---|
| | 44 | 45 | 46 | 47 | 17 | 18 | 19 |
| Tricalcium phosphate | 20.0 | 20.0 | 20.0 | 20.0 | 20.0 | 20.0 | 20.0 |
| Xanthan gum | 2.0 | 0.4 | 2.5 | 0.4 | 2.0 | 0.0 | 0.0 |
| Polyglycerin fatty acid ester | 1.0 | 0.1 | 1.0 | 3.0 | 0.0 | 1.0 | 0.0 |
| Soy milk | Balance | Balance | Balance | Balance | Balance | Balance | Balance |
| Viscosity (mPa · s) | 5030 | 1860 | 6500 | 2040 | 4980 | 1470 | 1390 |
| Dispersion stability evaluation | Excellent | Excellent | Good | Good | Fair | Poor | Poor |
| Redispersibility evaluation | Excellent | Excellent | Good | Fair | Poor | Poor | Poor |
| Usability | Good | Good | Fair | Fair | Poor | Poor | Poor |

In addition to the above evaluation tests on [Mouthwash], mouthwashes obtained by adding alkyldiaminoethylglycine hydrochloride to all of the mouthwashes non-supplemented with alkyldiaminoethylglycine hydrochloride (Examples 1 to 5, 8, 11, 13 to 16, 20, and as well as Comparative Examples 1 and 5) exhibited smaller alteration (precipitation, separation of water, etc.) and were observed to be more stable over time, compared with the mouthwashes non-supplemented therewith.

The invention claimed is:

1. A liquid oral composition comprising a calcium phosphate that is hydroxyapatite or tricalcium phosphate; a xanthan gum; a polyglycerin fatty acid ester; and an alkyldiaminoethylglycine hydrochloride, wherein a content of the calcium phosphate is 0.01 to 20.0% by weight with respect to the total composition, a content of the xanthan gum is 0.1 to 2.0% by weight with respect to the total composition, a content of the polyglycerin fatty acid ester is 0.01 to 2.5% by weight with respect to the total composition, and a content of the alkyldiaminoethylglycine hydrochloride is 0.01% to 0.15% by weight with respect to the total composition.

2. The liquid oral composition according to claim 1, wherein the liquid oral composition is obtained by adding the calcium phosphate into a solution in which the polyglycerin fatty acid ester is dissolved in an aqueous solvent, stirring the mixture, then adding the xanthan gum thereto, and stirring the mixture.

3. The liquid oral composition according to claim 1, wherein the liquid oral composition is obtained by adding the calcium phosphate and an amphoteric surfactant into a solution in which the polyglycerin fatty acid ester is dissolved in an aqueous solvent, stirring the mixture, then adding the xanthan gum thereto, and stirring the mixture.

4. The liquid oral composition according to claim 1, wherein the composition is a mouthwash, a liquid dentifrice, or a liquid food product.

* * * * *